United States Patent [19]

Zölffel et al.

[11] 4,456,778
[45] Jun. 26, 1984

[54] SEPARATING THE CHLORINATION PRODUCTS FROM THE REACTION GASES OBTAINED BY THE CHLORINATION OF METHANE AND METHYL CHLORIDE

[75] Inventors: Michael Zölffel, Marl; Johann Gaube, Roddorf, both of Fed. Rep. of Germany

[73] Assignee: Chemische Werke Huels Aktiengesellschaft, Marl, Fed. Rep. of Germany

[21] Appl. No.: 300,785

[22] Filed: Sep. 10, 1981

Related U.S. Application Data

[63] Continuation of Ser. No. 137,863, Apr. 7, 1980, abandoned, which is a continuation of Ser. No. 659,791, Feb. 12, 1976, abandoned.

[30] Foreign Application Priority Data

Feb. 21, 1975 [DE] Fed. Rep. of Germany ....... 2507505

[51] Int. Cl.$^3$ .............................................. C07C 17/10
[52] U.S. Cl. .................................... 570/255; 570/262
[58] Field of Search .............................. 570/255, 262

[56] References Cited

U.S. PATENT DOCUMENTS

| | | | |
|---|---|---|---|
| 1,975,727 | 10/1934 | Levine | 570/255 |
| 3,126,419 | 3/1964 | Burks et al. | 570/255 |
| 3,848,007 | 11/1974 | Forlano | 570/255 |
| 3,980,723 | 9/1976 | Riegel | 570/262 |
| 3,988,383 | 10/1976 | Huang et al. | 570/262 |
| 4,039,597 | 8/1977 | Tsao | 570/244 |

FOREIGN PATENT DOCUMENTS

| | | | |
|---|---|---|---|
| 1568575 | 12/1970 | Fed. Rep. of Germany | 570/262 |
| 40-2325 | 2/1965 | Japan | 570/262 |

OTHER PUBLICATIONS

Ullmann, "Encyclopadie der Technischen Chemie", 5, 406, 3rd Ed. (1954) TPU6. First Article Titled "Methanchlorierung ber den Chem. Werken Huls".

Primary Examiner—Charles F. Warren
Assistant Examiner—Joseph A. Boska
Attorney, Agent, or Firm—Millen & White

[57] ABSTRACT

The reaction gases from the chlorination of methane and preferably also methyl chloride, after removal of the HCl and drying, are subjected to the steps of partially condensing the dried stream of reaction gases at a pressure of 5-15 bars and at a temperature of 0°-40° C. which condenses the chloroform and the carbon tetrachloride; contacting the gaseous phase of the partially condensed stream of reaction gases in a countercurrent manner with a stream of liquid methyl chloride; recycling the stream of gases discharging from the contacting stream of liquid methyl chloride to the chlorination stage; and fractionating the contacting stream of liquid methyl chloride.

12 Claims, 3 Drawing Figures

1

SEPARATING THE CHLORINATION PRODUCTS FROM THE REACTION GASES OBTAINED BY THE CHLORINATION OF METHANE AND METHYL CHLORIDE

This is a continuation of application Ser. No. 137,863 filed Apr. 7, 1980, which in turn is a continuation of Ser. No. 659,791, filed Feb. 12, 1976 both abandoned.

BACKGROUND OF THE INVENTION

This invention relates to a process for separating the chlorination products from the reaction gases obtained by the chlorination of methane and methyl chloride.

In the manufacture of methyl chloride, methylene chloride, chloroform, and carbon tetrachloride, chlorine is reacted in the gaseous phase with excess methane and optionally also methyl chloride. Conventionally, the hydrogen chloride in the product gas stream formed during the chlorination is first separated by absorption with 20% strength hydrochloric acid and water and the remaining gas is then dried. The chlorinated hydrocarbons, in most cases, after compression of the gas are then condensed out of the product gas stream by cooling with cooling water and cooling brine, or they are washed out with low-temperature carbon tetrachloride and/or chloroform. Hydrocarbons are also utilized as absorption agents. Depending on the condensation temperature and amount of washing agent, a more or less large amount of methyl chloride remains in the gas which, after withdrawing a small amount of waste gas to prevent build-up of inert components, is recycled to the reactor as cycle gas. If a high yield of methylene chloride is desired, which is generally the case, no methylene chloride is left in the cycle gas, since it would otherwise be further chlorinated to chloroform and carbon tetrachloride. Since very often a higher proportion of methylene chloride is required than is obtained by the chlorination of methane, methyl chloride which had already been separated from the product gases by condensation or washing is recycled to the reactor after the distillative elimination of higher chlorinated components. Sometimes not only the entire methyl chloride produced by the chlorination but also extraneous methyl chloride obtained according to other processes, e.g., by reaction of hydrogen chloride with methanol, is fed to the chlorination reactor.

In the method of Farbwerke Hoechst (Ullmann, vol. 5, 1954, p. 404; Winnacker-Kuechler, "Chemische Technologie", vol. 4, 1972, p. 46), the reaction gas is first freed of the hydrogen chloride and then subjected to a low-temperature condensation. The gaseous stream leaving the condenser is recycled as cycle gas to the reactor after first branching off an exhaust gas stream to eliminate the inert components thereof. The condensed-out chlorinated hydrocarbons are then subjected to a distillation. Excess methyl chloride from the distillation plant, which is to be further chlorinated, is introduced into the cycle gas upstream of the reactor.

In the process according to Chemische Werke Huels AG. (Ullmann, vol. 5, 1954, p. 406; Winnacker-Kuechler, "Chemische Technologie," vol. 4, 1972, p. 46), the reaction gas, after separation of the hydrogen chloride, is compressed to about 8 bars, and is then condensed at about −13° C. The cycle gas is fed to the chlorination reactor in the same manner as in the method by Farbwerke Hoechst.

In the process in accordance with DOW Chemical Corp. (Ullmann, vol. 5, 1954, p. 406; Winnacker-Kuechler, vol. 4, 1972, p. 46), the chlorinated hydrocarbons are washed out of the reaction gas, prior to separation of the hydrogen chloride, by absorption with low-temperature-cooled chloroform and carbon tetrachloride. The low-chlorinated hydrocarbons are removed by distillation, then fed in the gaseous phase to a water washing stage in order to separate the hydrogen chloride, and then compressed and fractionated in a pressure distillation stage.

In another modification of working up the reaction gas described in German Published Application (DAS) No. 1,568,575, after cooling and compression, the reaction gas is scrubbed by washing with precooled, monochlorinated reaction products, in the case of a mixture of methane and methyl chloride, in one or two stages to separate the hydrogen chloride and the chlorinated hydrocarbons.

All of the above-mentioned processes have the feature in common that the condensation and/or absorption is conducted at low temperatures. When none or only a small amount of methyl chloride is desired as a product, the excess portion of the thus-condensed or absorbed methyl chloride must therefore be reevaporated and fed to the cycle gas upstream of the reactor. The advantage attained in the process according to DAS No. 1,568,575, viz., the direct production of dry hydrogen chloride, is confronted by considerable disadvantages, such as operating at low temperatures, higher pressures, and the compression of a gas containing hydrogen chloride, as well as, when methylene chloride is a desired reaction product, the energy-consuming evaporation of the thus-condensed methyl chloride.

Since methyl chloride can also be obtained in another, very simple process by reaction of methanol with hydrogen chloride (hydrochlorination), methyl chloride from this hydrochlorination in admixture with methane is used with increasing frequency as the starting material for producing methylene chloride and chloroform.

The present invention is directed to the problem of eliminating, insofar as possible, the disadvantage of the expensive condensation of methyl chloride and its subsequent evaporation, and especially avoiding the use of low temperatures without losing flexibility with regard to the product spectrum.

SUMMARY OF THE INVENTION

In the process of this invention, the reaction gases obtained by the chlorination of methane and methyl chloride, after removal of the hydrogen chloride and after drying, and containing methane, methyl chloride, methylene chloride, chloroform and carbon tetrachloride, are partially condensed at a pressure of 5–15 bars and a temperature of 0°–40° C. which condenses the chloroform and carbon tetrachloride and a portion of the methylene chloride, the gaseous phase remaining after the condensation, consisting predominantly of methane and methyl chloride, plus a portion of the methylene chloride, is fed to the lower section of a column charged with liquid methyl chloride; the gas withdrawn overhead from this column, consisting essentially of methane and methyl chloride is recycled to the chlorination stage, and the liquid mixture of sump product and condensate, is introduced into a fractionating zone, where methyl chloride is withdrawn overhead in the liquid phase. The sump product from the fractionating zone, containing all of the methylene chloride, chloroform, and carbon tetrachloride, can be introduced into a second fractionating zone and fractionated therein into its components.

BRIEF DESCRIPTION OF THE DRAWINGS

The process will be described hereinafter with reference to the drawings, in which.

DETAILED DISCUSSION

The chlorination of methane and methyl chloride is conducted in a conventional manner, e.g., as described in the publication cited above, whose disclosures are incorporated by reference.

Figure 1:
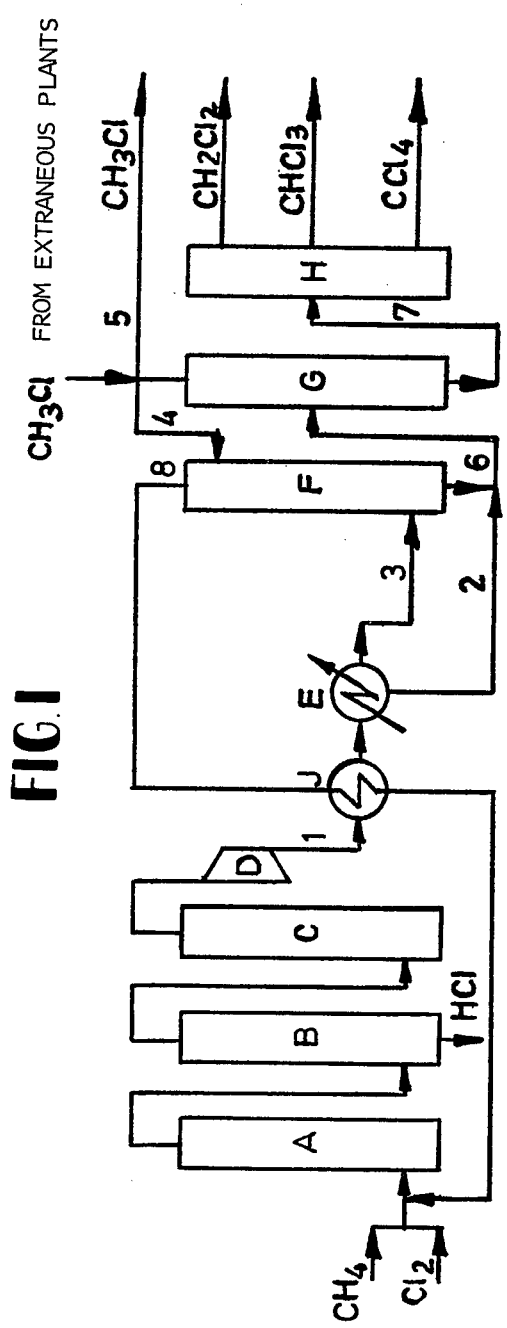
FIG. 1 is a schematic illustration of the process of this invention and equipment employed therein.

In the process illustrated schematically in FIG. 1, methane and methyl chloride are conventionally reacted in a reactor A with a less than stoichiometric amount of chlorine, e.g., 15% to 30% of stoichiometric amount. In a conventional manner, the thus-obtained reaction gases are passed into a scrubber B where they are washed, for example, with dilute hydrochloric acid, and thereby are freed of HCl, the latter being withdrawn. Also conventionally, in a dryer C, the moisture introduced by the scrubbing step into the reaction gas is removed.

The stream of dried and HCl-free reaction gas, which is the starting material for the process of this invention, is fed, e.g., at a temperature of 25°–40° C., to a compressor D where it is compressed to a pressure of 5–15 bars, preferably 8–12 bars. The compressed gas stream is passed in a conduit 1 into a condenser E where it is cooled to 0°–40° C., preferably 10°–30° C. During this step, partial condensation of the gas stream occurs. The gas phase of the condensed gas stream, consisting essentially of methane, methyl chloride, and part of the methylene chloride, is fed via a conduit 3 to a column F which is charged via a conduit 4 with liquid methyl chloride, e.g., at a temperature of 30° C. The liquid methyl chloride scrubs the methylene chloride from the gas stream with concurrent evaporation and cooling thereof. Gaseous methane and methyl chloride are discharged from the top of column F and are recycled to the chlorination stage via conduit 8. The liquid sump product in column F is discharged via a conduit 6, combined with the condensate from condenser E (product stream 2), and fed to a column G, where methyl chloride in the liquid phase is separated therefrom and withdrawn overhead and fed either via conduit 4 to column F or via a conduit 5 to the methyl chloride discharge point. The liquid sump product of column G contains all of the methylene chloride, chloroform, and carbon tetrachloride of the reaction product and is introduced via a conduit 7 to a separating plant H, where it is fractionated into its components.

The amount of liquid methyl chloride fed to column F via 4 depends on the amount of the methylene chloride entering column F and normally is 1.4 to 3 times the latter. The quantity of the methylene chloride remaining in the gaseous phase during the condensation depends, in turn, on the condensation conditions. If the condensation is vigorously conducted, i.e., if the cooling step is carried out at a low temperature under high pressure, within the above-mentioned ranges, only a small amount of methylene chloride remains in the gas, whereas the remainder, together with a considerable portion of the methyl chloride, passes into the condensate. In contradistinction, if the condensation is conducted under mild conditions, i.e., only slight cooling and/or lesser pressure is employed, then a large quantity of methylene chloride remains in the gas, whereas the smaller quantity passes into the condensate together with a small amount of methyl chloride. The magnitude of the condensation step employed depends on whether it is desired to withdraw methyl chloride via conduit 5; whether additional methyl chloride is to be directly recycled into the cycle via conduit 4; or whether only the amount corresponding to the quantity of methylene chloride in column F is to be withdrawn in column G via conduit 4. Under industrial conditions, the ratios in column F can be regulated in a simple fashion by observing the occurrence of methylene chloride at the head of column F and adjusting the cooling efficiency of the condenser E so that the point is attained where no methylene chloride appears. The process can be made even more flexible if liquid methyl chloride from other plants, obtained, for example, from the hydrogen chloride produced in scrubber B by conventional reaction with methanol, is introduced into conduit 4. It then is possible to conduct only a slight condensation, i.e., to introduce a large amount of methylene chloride via conduit 3 into column F, although in such a case less methyl chloride passes with the condensate via conduits 2 and 6 to column G than is required for separating the methylene chloride in column F. The gases withdrawn overhead from column F and consisting predominantly of methane and methyl chloride have a temperature of −10° to +17° C. as a result of the evaporation of the liquid methyl chloride in column F. This cooling value can be utilized if recycle 8 is conducted via the heat exchanger J wherein a heat exchange takes place with the reaction gases leaving the compressor via conduit 1.

A heat exchange of recycle gases 8 with the gases in conduit 1 is particularly useful if liquid methyl chloride from extraneous plants is employed. In such a case, the evaporative cold of the methyl chloride from the extraneous plants can be utilized in heat exchanger J.

Figure 2:
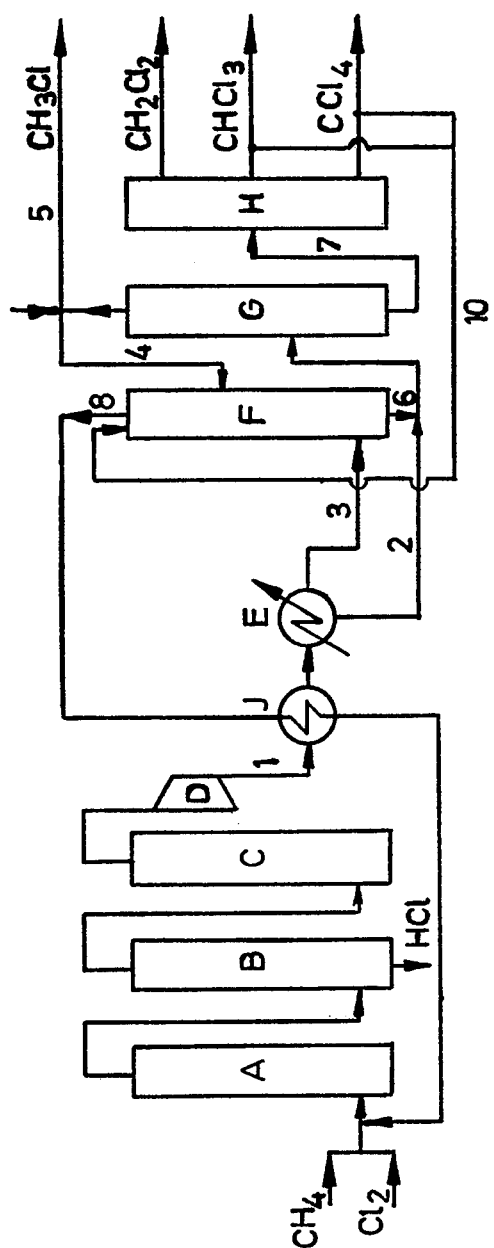
FIG. 2 is a schematic illustration of a preferred embodiment of the process of this invention.

FIG. 2 illustrates an advantageous embodiment wherein a partial stream of chloroform and/or carbon tetrachloride, suitably ⅛ to ¼ of the amount separated in separating unit H, is introduced into the head of column F via conduit 10. In this embodiment, the liquid methyl chloride is fed to column F via conduit 4, suitably in the middle third section thereof. Column F then acts as an absorber wherein methylene chloride is absorbed by chloroform and/or by carbon tetrachloride. A smaller amount of liquid methyl chloride is required, and only lower cooling efficiency is necessary in condenser E. Accordingly, the temperature in column F and especially the temperature of the gases leaving column F by way of conduit 8 are higher. In this way, condensation energy is saved and a simple river water cooling is adequate.

Figure 3:
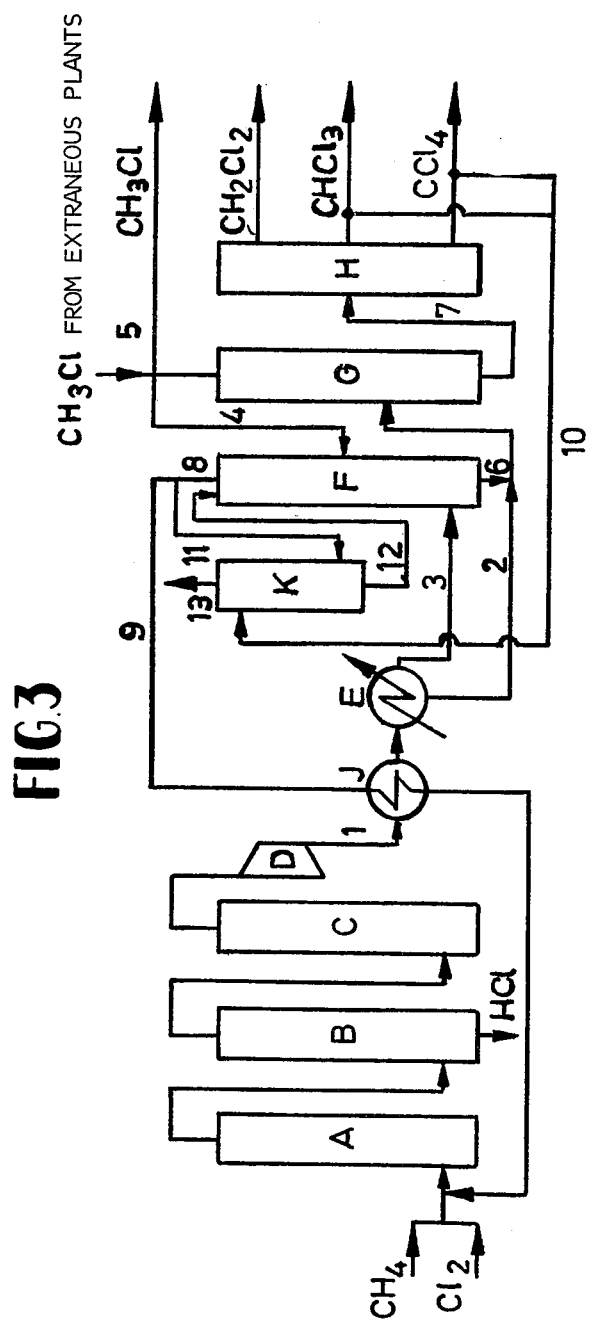
FIG. 3 is a schematic illustration of an especially preferred embodiment of the process of this invention.

A particularly advantageous embodiment is shown in FIG. 3. To avoid an enrichment of the cycle gas with inert substances entrained with the reaction components, an amount of gas is withdrawn from the cycle gas at conduit 8 such that the inert gas level in the cycle gas 9 does not exceed 10–30%. This withdrawn gaseous stream is then fed to an absorber K via conduit 11 where it is conducted countercurrently to the chloroform and- /or carbon tetrachloride introduced at the head via conduit 10, whereby the gaseous stream is extensively freed of methyl chloride and then leaves the plant as waste gas via conduit 13. In order to keep at a minimum the amounts of methyl chloride, chloroform and/or carbon tetrachloride, discharged in accordance with the pressure along with the waste gas and thus minimize environmental pollution, it can be advantageous to cool chloroform and/or carbon tetrachloride to temperatures of 10° to −10° C. before their introduction into the absorber. The chloroform and/or carbon tetrachloride, loaded with methyl chloride, is conducted from absorber K via conduit 12 to the head of column F. Normally, the same amount is employed as can also be introduced directly into column F. To exclude avoidable pollution of the environment, this amount generally should not fall below 0.3 kg./Nm³ of waste gas.

The above-described measures attain their highest effectiveness with maximum methylene chloride production. Moreover, because of these measures, the required flexibility of the plant is not limited. It is still possible, by operating the condenser at low temperatures, to achieve higher methyl chloride production. Higher production of chloroform is also possible by leaving methylene chloride in the recycle gas.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the tables below, the contents of the substance streams, denoted in accordance with the associated conduits, are given in moles per mole of reaction gas (substance stream 1). Where dashes are indicated, the content is 0.001 mole. In substance streams 2 and 6, a small amount of methane is present which is withdrawn at the head of column G and added to the cycle gas stream 9.

The values given in the Examples hereinafter are typical of those obtained by passing a stream of about 43 kml/hr. of methane plus methyl chloride plus 15 Vol% inert components and 12.5 kml/hr. of chlorine gas into a reactor maintained at 550° C. and 1.5 bars pressure.

After removing hydrogen chloride from and then drying the reaction gases, the dried gases are compressed at a pressure and cooled to a temperature which condenses all of the chloroform and carbon tetrachloride and at least some, e.g., 65% of the methylene chloride, e.g., about 9 bars and about 30° C. Cooling in the examples is achieved in the preferred manner in stages, viz., first by indirect countercurrent heat exchange with methane and methyl chloride being recycled to the chlorination stage and then by indirect countercurrent heat exchange with cooling water. The liquid phase of the partially condensed reaction gases is then conducted to a fractionation stage; where the various chlorinated products are separated. The 37 kml/hr. of gaseous phase is scrubbed in a countercurrent manner at 10°–30° C. with 2.3 kml/hr. of liquid methyl chloride. The 36.1 kml/hr. of gases exiting from the scrubbing towers is recycled to the chlorination stage and the 3.5 kml/hr. of sump liquid is combined with the liquid phase of the partially condensed reaction gases to provide 6.4 kml/hr. of liquid chlorinated products going to the fractionation stage, yielding 3.9 kml/hr. of methylene chloride, 1.9 kml/hr. of chloroform and 0.6 kml/hr. of carbon tetrachloride. 0.5 kml/hr. of methyl chloride is also withdrawn.

EXAMPLE 1

In this example, (Table 1; FIG. 1), the gas (substance stream 3) leaving condenser E flows into column F countercurrently to liquid methyl chloride entering by conduit 4 and leaving by conduit 6. The condenser temperature required to separate the methylene chloride from gaseous stream 3 at a pressure of 8 bars is 17° C. If, in accordance with the state of the art, column F is omitted, the condensation temperature must be −25° C. in order to obtain the same degree of separation of methylene chloride from gaseous stream 3.

EXAMPLE 2

In this example, (Table 2; FIG. 2), column F is charged at its head with a mixture of chloroform and carbon tetrachloride and liquid methyl chloride is fed to the middle of the column. The condenser temperature can then be set at 30° C., thus permitting water to be used for cooling purposes.

EXAMPLE 3

In this example (Table 3; FIG. 3), the mixture of chloroform and carbon tetrachloride, cooled to −10° C., is first fed to absorber K for scrubbing out the methyl chloride contained in the branched-off gaseous stream 11. The discharge stream 12 from absorber K is introduced to the head of column F.

TABLE 1

| | EXAMPLE 1 | | | | | |
|---|---|---|---|---|---|---|
| | $CH_4$ | INERT SUBSTANCES | $CH_3Cl$ | $CH_2Cl_2$ | $CHCl_3$ | $CCl_4$ |
| Substance Stream 1 | 0.4927 | 0.1513 | 0.2220 | 0.0917 | 0.0382 | 0.0041 |
| Substance Stream 2 | | | 0.0706 | 0.0750 | 0.0334 | 0.0035 |
| Substance Stream 3 | 0.4927 | 0.1513 | 0.1514 | 0.0167 | 0.0048 | 0.0006 |
| Substance Stream 4 | — | — | 0.0796 | — | — | — |
| Substance Stream 5 | — | — | 0.0026 | — | — | — |
| Substance Stream 6 | | | 0.0116 | 0.0147 | 0.0048 | 0.0006 |
| Substance Stream 7 | — | — | — | 0.0897 | 0.0382 | 0.0041 |
| Substance Stream 8 | 0.4927 | 0.1513 | 0.2194 | 0.0020 | — | — |
| Condenser Temperature | | | 17° C. | | | |
| Pressure | | | 9 bars | | | |

TABLE 2

EXAMPLE 2

|  | CH$_4$ | INERT SUBSTANCES | CH$_3$Cl | CH$_2$Cl$_2$ | CHCl$_3$ | CCl$_4$ |
| --- | --- | --- | --- | --- | --- | --- |
| Substance Stream 1 | 0.4810 | 0.1474 | 0.2220 | 0.0917 | 0.0492 | 0.0087 |
| Substance Stream 2 |  |  | 0.0417 | 0.0600 | 0.0391 | 0.0073 |
| Substance Stream 3 | 0.4810 | 0.1474 | 0.1803 | 0.0317 | 0.0101 | 0.0014 |
| Substance Stream 4 | — | — | 0.0534 | — | — | — |
| Substance Stream 5 | — | — | 0.0026 | — | — | — |
| Substance Stream 6 |  |  | 0.0143 | 0.0297 | 0.0163 | 0.0113 |
| Substance Stream 7 | — | — | — | 0.0897 | 0.0554 | 0.0186 |
| Substance Stream 8 | 0.4810 | 0.1474 | 0.2194 | 0.0020 | 0.0113 | 0.0057 |
| Substance Stream 10 | — | — | — | — | 0.0175 | 0.0156 |
| Condenser Temperature |  |  | 30° C. |  |  |  |
| Pressure |  |  | 9 bars |  |  |  |

TABLE 3

EXAMPLE 3

|  | CH$_4$ | INERT SUBSTANCES | CH$_3$Cl | CH$_2$Cl$_3$ | CHCl$_3$ | CCl$_4$ |
| --- | --- | --- | --- | --- | --- | --- |
| Substance Stream 1 | 0.4810 | 0.1474 | 0.2220 | 0.0917 | 0.0492 | 0.0087 |
| Substance Stream 2 |  |  | 0.0417 | 0.0600 | 0.0391 | 0.0073 |
| Substance Stream 3 | 0.4810 | 0.1474 | 0.1803 | 0.0317 | 0.0101 | 0.0014 |
| Substance Stream 4 | — | — | 0.0534 | — | — | — |
| Substance Stream 5 | — | — | 0.0103 | — | — | — |
| Substance Stream 6 |  |  | 0.0220 | 0.0297 | 0.0166 | 0.0113 |
| Substance Stream 7 | — | — | — | 0.0897 | 0.0557 | 0.0186 |
| Substance Stream 8 | 0.4810 | 0.1474 | 0.2194 | 0.0020 | 0.0113 | 0.0057 |
| Substance Stream 9 | 0.4604 | 0.1411 | 0.2117 | 0.0020 | 0.0109 | 0.0057 |
| Substance Stream 10 | — | — | — | — | 0.0175 | 0.0156 |
| Substance Stream 11 | 0.0206 | 0.0063 | 0.0077 | — | 0.0004 | — |
| Substance Stream 12 | — | — | 0.0077 | — | 0.0178 | 0.0156 |
| Substance Stream 13 | 0.0206 | 0.0063 | — | — | 0.0001 | — |
| Condenser Temperature |  |  | 30° C. |  |  |  |
| Pressure |  |  | 9 bars |  |  |  |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a continuous process for chlorinating a mixture of methane and methyl chloride, and maximizing the yield of methylene chloride, wherein a mixture of methane and methyl chloride is reacted with chlorine in the gas phase; the effluent gas stream is freed of HCl; the HCl-free stream is dried; and the dry, HCl-free effluent gas stream is fractionated to obtain: a recycle gas stream, consisting essentially of methane and methyl chloride, which is recycled to the chlorination step; and a liquid product stream, containing methyl chloride, substantially all of the methylene chloride produced in the reaction, chloroform and carbon tetrachloride, said liquid product stream being further fractionated into its components, including a methylene chloride product stream, the improvement which comprises (a) cooling said dry, HCl-free effluent gas stream by indirect heat exchange, at a pressure of 5-15 bars, to a temperature of 10°-40° C., thereby effecting a partial condensation thereof, and recovering (i) a residual gaseous stream containing methylene chloride and predominating in methane and methyl chloride, and (ii) a liquid condensate stream containing methyl chloride, methylene chloride, chloroform and carbon tetrachloride;

(b) contacting said residual gaseous stream (i) from step (a) countercurrently with a stream of liquid methyl chloride having an inlet temperature of about 30° C., in the absence of external indirect cooling, the amount of said liquid methyl chloride stream being from 1.4 to 3 times the amount of methylene chloride in said residual gaseous stream, whereby vaporization of liquid methyl chloride, direct internal cooling of the gas stream and condensation of gaseous methylene chloride are effected, thereby incorporating substantially all the methylene chloride from said residual gaseous stream into the liquid phase, and recovering (iii) a gas stream which is recycled as said recycle gas stream, and (iv) a liquid phase stream;

(c) combining said liquid condensate stream (ii) from step (a) with said liquid phase stream (iv) from step (b) to form said liquid product stream; and (d) fractionating said liquid product stream from step (c) and recovering a liquid methyl chloride stream, at least a portion of which is recycled to step (b), and a sump product stream which is further fractionated into its component product streams including said methylene chloride product stream.

2. In a continuous process for chlorinating a mixture of methane and methyl chloride, and maximizing the yield of methylene chloride, wherein a mixture of methane and methyl chloride is reacted with chlorine in the gas phase; the effluent gas stream is freed of HCl; the HCl-free stream is dried; and the dry, HCl-free effluent gas stream is fractionated to obtain: a recycle gas stream, consisting essentially of methane and methyl chloride, which is recycled to the chlorination step; and a liquid product stream, containing methyl chloride, substantially all of the methylene chloride produced in the reaction, chloroform and carbon tetrachloride, said liquid product stream being further fractionated into its components, including a methylene chloride product stream the improvement which comprises (a) cooling said dry, HCl-free effluent gas stream by indirect heat exchange, at a pressure of 5–15 bars, to a temperature of 10°–40° C., thereby effecting a partial condensation thereof, and recovering (i) a residual gaseous stream containing methylene chloride and predominating in methane and methyl chloride, and (ii) a liquid condensate stream containing methyl chloride, methylene chloride, chloroform and carbon tetrachloride:

(b) contacting said residual gaseous stream (i) from step (a) countercurrently in a column, in the absence of external indirect cooling, with a liquid stream of at least one of chloroform and carbon tetrachloride introduced at the head of said column, and introducing a stream of liquid methyl chloride in the middle third of said column and at an inlet temperature of about 30° C., whereby vaporization of liquid methyl chloride, direct internal cooling of the gas stream, and condensation of gaseous methylene chloride are effected, at 10°–30° C., thereby incorporating substantially all the methylene chloride from said residual gaseous stream into the liquid phase, and recovering (iii) a gas stream which is recycled as said recycle gas stream, and (iv) a liquid phase stream;

(c) combining said liquid condensate stream (ii) from step (a) with said liquid phase stream (iv) from step (b) to form said liquid product stream; and (d) fractionating said liquid product stream from step (c) and recovering a liquid methyl chloride stream, at least a portion of which is recycled to step (b), and a sump product stream which is further fractionated into its component product streams including said methylene chloride product stream.

3. A process according to claim 2, wherein in step (a), the cooling of said dry, HCl-free effluent gas stream is effected by first passing the stream in indirect countercurrent heat exchange with said recycle gas stream (iii) from step (b) before the latter is recycled to the chlorination stage, and then by passing the partially cooled stream in indirect countercurrent heat exchange with cooling water.

4. A process according to claim 2, wherein in step (a), said dry, HCl-free effluent gas stream is partially condensed at a pressure of about 9 bars and a temperature of about 30° C.

5. A process according to claim 2, wherein in step (a), said dry, HCl-free effluent gas stream is partially condensed at a temperature of 10°–30° C.

6. A process according to claim 2, wherein in step (b), the liquid stream of at least one of chloroform and carbon tetrachloride is obtained from a portion of at least one of a liquid chloroform product stream and a liquid carbon tetrachloride product stream recovered in step (d).

7. In a continuous process for chlorinating a mixture of methane and methyl chloride, and maximizing the yield of methylene chloride, wherein a mixture of methane and methyl chloride is reacted with chlorine in the gas phase; the effluent gas stream is freed of HCl; the HCl-free stream is dried; and the dry, HCl-free effluent gas stream is fractionated to obtain: a recycle gas stream, consisting essentially of methane and methyl chloride, which is recycled to the chlorination step; and a liquid product stream, containing methyl chloride, substantially all of the methylene chloride produced in the reaction, chloroform and carbon tetrachloride, said liquid product stream being further fractionated into its components, including a methylene chloride product steam, the improvement which comprises (a) cooling said dry, HCl-free effluent gas stream by indirect heat exchange, at a pressure of 5–15 bars, to a temperature of 10°–40° C., thereby effecting a partial condensation thereof, and recovering (i) a residual gaseous stream containing methylene chloride and predominating in methane and methyl chloride, and (ii) a liquid condensate stream containing methyl chloride, methylene chloride, chloroform and carbon tetrachloride:

(b) contacting said residual gaseous stream (i) from step (a) countercurrently in a column, in the absence of external indirect cooling, with a rich liquid scrub stream as hereinafter defined, introduced at the head of said column, and introducing a stream of liquid methyl chloride in the middle third of said column and at an inlet temperature of about 30° C., whereby vaporization of liquid methyl chloride, direct internal cooling of the gas stream, and condensation of gaseous methyl chloride are effected at 10°–30° C., thereby incorporating substantially all the methylene chloride from said residual gaseous stream into the liquid phase, and recovering (iii) a substantially methylene chloride-free gas stream, and (iv) a liquid phase stream;

(c) dividing said substantially methylene chloride-free gas stream (iii) from step (b) into a first gas stream and a second gas stream, the first gas stream being recycled to the chlorination stage as said recycle gas stream; scrubbing said second gas stream with a liquid scrub stream of at least one of chloroform and carbon tetrachloride to effect incorporation of substantially all of the methyl chloride from the second gas stream into the scrubbing liquid, and recovering (v) a waste gas stream, and (vi) a rich liquid scrub stream which is recycled to step (b); the relative proportions of said first gas stream and said second gas stream being such as to maintain the inert gas content in said recycle gas stream at a level not exceeding 10–30% by volume;

(d) combining said liquid condensate stream (ii) from step (a) with said liquid phase stream (iv) from step (b) to form said liquid product stream; and (e) fractionating said liquid product stream from step (d) and recovering a liquid methyl chloride stream, at least a portion of which is recycled to step (b), and a sump product stream which is further fractionated into its component product streams including said methylene chloride product stream.

8. A process according to claim 7, wherein in step (a), the cooling of said dry, HCl-free effluent gas stream is effected by first passing the stream in indirect countercurrent heat exchange with said recycle gas stream (iii) from step (b) before the latter is recycled to the chlorination stage, and then by passing the partially cooled stream in indirect countercurrent heat exchange with cooling water.

9. A process according to claim 7 wherein in step (a), said dry, HCl-free effluent gas stream is partially condensed at a pressure of about 9 bars and a temperature of about 30° C.

10. A process according to claim 7 wherein in step (c), the liquid stream of at least one of chloroform and carbon tetrachloride is obtained from a portion of at least one of a liquid chloroform product stream and a liquid carbon tetrachloride product stream recovered in step (e).

11. A process according to claim 7 wherein in step (a), said dry, HCl-free effluent gas stream is partially condensed at a temperature of 10°–30° C.

12. A process according to claim 7, wherein in step (c), said liquid scrub stream is cooled to a temperature of from −10° to 10° C. prior to contacting said second gas stream.

* * * * *